| United States Patent [19] | [11] Patent Number: 4,743,586 |
| Chan | [45] Date of Patent: May 10, 1988 |

[54] METHOD OF TREATING HYPERTENSION USING SUBSTITUTED IMIDAZO[1,5-D]1,2,4-TRIAZIN-1(2H)-ONES

[75] Inventor: Peter S. Chan, Suffern, N.Y.

[73] Assignee: American Cyanamid Company, Stamford, Conn.

[21] Appl. No.: 924,395

[22] Filed: Oct. 29, 1986

[51] Int. Cl.$^4$ .................. A61K 31/53; C07D 487/04; C07D 401/14
[52] U.S. Cl. ..................................... 514/243; 544/184
[58] Field of Search ..................... 544/184; 514/243

[56] References Cited

U.S. PATENT DOCUMENTS 4,107,307  8/1978  Paul et al. ............................ 544/184
4,115,572  9/1978  Paul et al. ............................ 544/184

OTHER PUBLICATIONS

Chem. Abstracts, vol. 90, Abstract No. 90:49648q, (1979).

Primary Examiner—John M. Ford
Assistant Examiner—Zinna Northington
Attorney, Agent, or Firm—E. A. Conroy

[57] ABSTRACT

This disclosure describes compositions of matter containing certain substituted imidazo[1,5-d]-1,2,4-triazin-1(2H)-ones and the method of treating hypertension therewith.

13 Claims, No Drawings

METHOD OF TREATING HYPERTENSION USING SUBSTITUTED IMIDAZO[1,5-D]1,2,4-TRIAZIN-1(2H)-ONES

SUMMARY OF THE INVENTION

This invention is concerned with a method of treating hypertension in mammals by the administration of a compound selected from those of the formula:

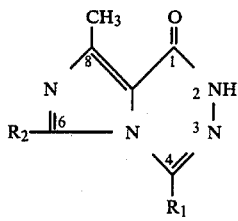

wherein $R_1$ is selected from the group consisting of hydrogen and alkyl($C_1$-$C_3$) and $R_2$ is selected from the group consisting of hydrogen, 2-pyridinyl, 3-pyridinyl, 1-naphthalenyl and 4-methylphenyl.

BACKGROUND OF THE INVENTION

Compounds of the above formula where $R_1$ is alkyl($C_1$-$C_3$) and $R_2$ is hydrogen are disclosed generically in U.S. Pat. No. 4,115,572 as anti-asthmatic agents. Specifically these compounds are 4-ethyl-8-methylimidazo[1,5-d]-1,2,4-triazin-1(2H)-one and 8-methyl-4-propylimidazo[1,5-d]-1,2,4-triazin-1,(2H)-one.

Compounds of the above formula where $R_1$ is hydrogen and $R_2$ is other then hydrogen are considered new compounds which are not disclosed in any U.S. patent. Specifically these compounds are:

8-methyl-6-(3-pyridinyl)imidazo[1,5-d]-1,2,4-triazin-1-(2H)-one 8-methyl-6-(1-naphthalenyl)imidazo[1,5-d]-1,2,4-triazin-1-(2H)-one 8-methyl-6-(2-pyridinyl)imidazo[1,5-d]-1,2,4-triazin-1-(2H)-one 8-methyl-6-(4-methylphenyl)imidazo[1,5-d]-1,2,4-triazin-1-(2H)-one These compounds may be prepared by the procedure shown in the following flowchart.

FLOWCHART

In accordance with the above flowchart a methylamine 1, where $R_3$ is 2-pyridinyl, 3-pyridinyl, 1-naphthalenyl or 4-methylphenyl is reacted with 2,3-dioxobutyric acid, ethyl ester, (Z)-2-oxime 2 at reflux temperature giving 3, which is reacted with anhydrous hydrazine, giving hydrazide 4, which is then reacted with triethoxymethane at reflux, giving the product 4.

DESCRIPTION OF THE INVENTION

The compounds of the present invention are active hypotensive agents as established in the following test described by P. S. Chan and D. W. Poorvin, Clinical and Experimental Hypertension, 1(6), 817-830 (1979). Male, 16 week old, spontaneously hypertensive rats of the Okamoto strain, having an average mean arterial blood pressure (MABP) of 160±1.5 mm of mercury, are used in this test. One to three rats are used per test compound. A rat is dosed by gavage with a test compound, suspended in 2% preboiled starch, at a concentration of 50 mg/ml, at the indicated dose, with 0.9% sodium chloride loading at a dose of 25 ml/kg of body weight. A second identical dose of the test compound, without sodium chloride loading, is given 24 hours later. At 28 hours after the initial dose the mean arterial blood pressure is measured. The procedure is repeated in a second and third rat when necessary.

The results of this test on representative compounds of this invention appear in Table I.

TABLE I

| | Hypotensive Activity | | |
|---|---|---|---|
| Compound | Dose (mg/kg) | MABP (mmHg) | No. of Rats |
| 4-Ethyl-8-methylimidazo[1,5-d]-1,2,4-triazin-1(2H)—one | 100 | 119 | 2 |
| 8-Methyl-4-propylimidazo[1,5-d]-1,2,4-triazin-1(2H)—one | 100 | 104 | 2 |
| 8-Methyl-6-(3-pyridinyl)imidazo-[1,5-d]-1,2,4-triazin-1(2H)—one | 50 | 91 | 2 |
| 8-Methyl-6-(1-naphthalenyl)-imidazo[1,5-d]-1,2,4-triazin-1(2H)—one | 30 | 139 | 2 |
| 8-Methyl-6-(2-pyridinyl)imidazo-[1,5-d]-1,2,4-triazin-1(2H)—one | 100 | 130 | 3 |
| 8-Methyl-6-(4-methylphenyl)-imidazo[1,5-d]-1,2,4-triazin- | 100 | 136 | 2 |

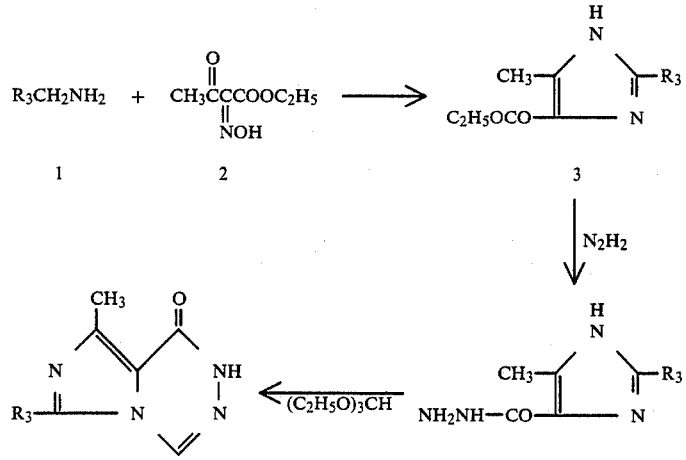

TABLE I-continued

| Compound | Hypotensive Activity | | |
|---|---|---|---|
| | Dose (mg/kg) | MABP (mmHg) | No. of Rats |
| 1(2H)—one | | | |

The compounds of this invention have thus been found to be highly useful for treating hypertension in mammals when administered in amounts ranging from about 5 mg to about 100 mg per kilogram of body weight per day. Such dosage units are employed that a total of from about 0.35 g to about 3.5 g of active compound for a subject of about 70 kg of body weight are administered in a 24 hour period. The dosage regimen may be adjusted to provide the optimum therapeutic response. For example, several divided doses may be administered daily or the dose may be proportionally reduced as indicated by the exigencies of the therapeutic situation. A decided practical advantage is that these compounds may be administered by the oral route, for example, with an inert diluent or with an assimilable edible carrier, or they may be enclosed in hard or soft shell gelatin capsules, or they may be compressed into tablets, or they may be incorporated directly with the food of the diet.

For oral therapeutic administration, the active compounds may be incorporated with excipients and used in the form of tablets, capsules, elixirs, suspensions, syrups and the like. Such compositions and preparations should contain at least 0.1% of active compound and normally varies between 2 and 60% of the weight of the unit, such that a suitable dosage is obtained.

The tablets, capsules and the like may also contain a binder such as gum tragacanth, accacia, corn starch or gelatin; excipients such as dicalcium phosphate; a disintegrating agent such as alginic acid; a lubricating agent such as magnesium stearate; and a sweetening agent such as sucrose, lactose or saccharin or a flavoring agent such as peppermint, oil of wintergreen or cherry flavoring.

When the dosage unit is a capsule it may contain, in addition to materials of the above-type, a liquid carrier such as a fatty oil.

Various other materials may be present as coatings or to otherwise modify the physical form of the dosage unit. For instance, tablets or capsules may be coated with shellac, sugar or both. A syrup or elixir may contain the active compound, sucrose as a sweetening agent, methyl and propylparabens as preservatives, a dye and flavoring such as cherry or orange flavor.

All materials used must be pharmaceutically pure and substantially non-toxic in the amounts employed.

EXAMPLE 1

4-Ethyl-8-methylimidazo[1,5-d]-1,2,4-triazin-1(2H)-one

To a hot solution of 154 g of 5-methyl-1H-imidazole-4-carboxylic acid, ethyl ester in 2 liters of absolute ethanol was added dropwise, but rapidly, 100 g of hydrazine hydrate. The solution was stirred at reflux temperature for 3 hours, then 150 ml of hydrazine hydrate was added and the solution was refluxed for 3 days. The mixture was partially evaporated, the solid collected, washed twice with absolute ethanol, then ether and dried, giving 121.3 g of 5-methyl-1H-imidazole-4-carboxylic acid hydrazide.

A mixture of 10 g of the above hydrazide and 80 ml of triethyl ortho propionate in 395 ml of absolute ethanol was stirred at reflux temperature for 24 hours, then the solvent was removed in vacuo and the solid was triturated with petroleum ether and collected, giving 15.6 g of 5-methyl-4-imidazolecarboxylic acid, 2-(1-ethoxypropylidene)hydrazide.

A 15 g portion of this hydrazide in 200 ml of diphenyl ether was stirred in an oil bath at 240°-250° C. for 15 minutes, then cooled and allowed to stand overnight. The solid was collected, washed repeatedly with petroleum ether and dried, giving 11.3 g of the desired product, mp 175°-178° C.

EXAMPLE 2

8-Methyl-4-propylimidazo[1,5-d]-1,2,4-triazin-1(2H)-one

A mixture of 10 g of 5-methyl-1H-imidazole-4-carboxylic acid hydrazide, 80 ml of trimethylorthobutyrate and 395 ml of absolute ethanol was treated and described in Example 1, giving 16.5 g of 5-methyl-4-imidazolecarboxylic acid, 2-(1-methoxybutylidene)hydrazide.

A 16 g portion of this hydrazide was reacted with 200 ml of diphenyl ether as described in Example 1, giving 12.3 g of the desired product, mp 168°-170° C.

EXAMPLE 3

8-Methyl-6-(3-pyridinyl)imidazo[1,5-d]-1,2,4-triazin-1(2H)-one

A 50 g portion of ethyl acetoacetate in 60 ml of acetic acid was stirred at 0° C. to 10° C., as a solution of 30 g of sodium nitrite in 50 ml of water was added dropwise. When addition was complete, the mixture was stirred at 0° to 10° C. for 30 minutes and then diluted with 300 ml of ice water. The mixture was stirred for 2 hours and then extracted with 500 ml of dichloromethane. The dichloromethane layer was separated, washed with two 500 ml portions of ice water, dried, filtered and evaporated in vacuo. The residual oil was stirred vigorously with 200 ml of hexane and the resulting solid collected, washed with hexane and air dried, giving 31.4 g of 2,3-dioxobutyric acid, ethyl ester, (Z)-2-oxime.

A solution of 16 g of 2,3-dioxobutyric acid ethyl ester, (Z)-2-oxime, 12 g of 3-aminomethylpyridine and 100 ml of acetonitrile was stirred at reflux for 4 hours, then clarified while hot and the filtrate cooled at −10° C. The resulting precipitate was collected, washed with acetonitrile, air dried and recrystallized from acetonitrile at −10° C., giving 4.8 g of 5-methyl-2-(3-pyridinyl)-1H-imidazole-4-carboxylic acid, ethyl ester.

A solution of 32 g of 5-methyl-2-(3-pyridinyl)-1H-imidazole-4-carboxylic acid, ethyl ester (prepared as described above) in ethanol was heated to boiling. A 79 ml portion of hydrazine was added. This mixture was stirred at reflux for 14 hours and then cooled to −10° C. The mixture was taken to dryness in vacuo and then evaporated to dryness in vacuo twice from 125 ml portions of methyl cellosolve. The residue was shaken with 100 ml of ethanol and the solids collected, washed with 100 ml of ethanol and two 100 ml portions of ether and dried at 60° C. in vacuo, giving 18.7 g of 5-methyl-2-(3-pyridinyl)-1H-imidazole-4-carboxylic acid, hydrazide.

A 5 g portion of 5-methyl-2-(3-pyridinyl)-1H-imidazole-4-carboxylic acid, hydrazide in 100 ml of triethoxymethane was stirred at reflux for 18 hours in an oil bath at 220° C. The volatiles were boiled off as the temperature of the oil bath rose to 250°-260° C. The residue in the flask melted, then solidified, was kept at 250°-260° C. for 30 minutes and then cooled to room temperature. The solid was boiled in 200 ml of ethanol, the solid collected, dissolved in 100 ml of boiling methyl cellosolve, treated with charcoal and clarified. The filtrate was cooled at −5° C., the solid collected washed with ethanol and dried, giving 600 mg of the desired product, mp 292°-295° C. (dec.).

EXAMPLE 4

8-Methyl-6-(1-naphthalenyl)imidazo[1,5-d]-1,2,4-triazin-1(2H)-one

A mixture of 9.1 g of 1-naphthalenemethylamine, 8.4 g of 2,3-dioxobutyric acid, ethyl ester, (Z)-2-oxime and 115 ml of acetonitrile was refluxed for 5 hours and then cooled. The solid was collected, giving 7.0 g of 5-methyl-2-(1-naphthalenyl)-1H-imidazole-4-carboxylic acid, ethyl ester.

A mixture of 5.0 g of the above ester and 25 ml of hydrazine was refluxed overnight and then cooled. The solid was collected, stirred with water and cooled. The solid was collected, giving 4.5 g of 5-methyl-2-(1-naphthalenyl)-1H-imidazole-4-carboxylic acid, hydrazide.

A mixture of 3.5 g of the above hydrazide and 15 ml of triethoxymethane was refluxed overnight, then cooled in ice and the solid collected. This solid was recrystallized from hot ethanol with charcoal treatment, giving 300 mg of the desired product, mp 261°-263° C.

EXAMPLE 5

8-Methyl-6-(2-pyridinyl)imidazo[1,5-d]-1,2,4-triazin-1(2H)-one

A mixture of 23.8 g of 2,3-dioxobutyric acid, ethyl ester, (Z)-2-oxime, 18 g of 2-aminomethyl pyridine and 250 ml of acetonitrile was refluxed for 7 hours and then stored at −10° C. overnight. The solid was collected, giving 20.68 g of 5-methyl-2-(2-pyridinyl)-1H-imidazole-3-carboxylic acid, ethyl ester.

A mixture of 18.2 g of the above ester and 55 ml of hydrazine was refluxed overnight, then cooled in an ice bath. The solid was collected, giving 13 g of 5-methyl-2-(2-pyridinyl)-1H-imidazole-4-carboxylic acid, hydrazide.

A mixture of 10.5 g of the above hydrazide and 56 ml of triethylorthoformate was stirred and refluxed overnight, then cooled in an ice bath. The solid was collected and recrystallized from ether, giving 8.5 g of solid. A 7.0 g portion of this solid was heated at 270°-275° C. and then recrystallized from ethanol, giving 4.5 g of the desired product, mp 295°-297° C.

EXAMPLE 6

8-Methyl-6-(4-methylphenyl)imidazo[1,5-d]-1,2,4-triazin-1(2H)-one

A mixture of 10.7 g of 4-methylbenzylamine, 12.7 g of 2,3-dioxobutyric acid, ethyl ester, (Z)-2-oxime and 160 ml of acetonitrile was stirred and refluxed for 3.5 hours. The mixture was cooled, the solid collected and recrystallized from ethanol, giving 6.2 g of 5-methyl-2-(4-methylphenyl)-1H-imidazole-4-carboxylic acid, ethyl ester.

A mixture of 4.9 g of the above ester and 15 ml of anhydrous hydrazine was stirred and refluxed overnight. Water was added, the mixture was evaporated and the residue recrystallized from ethanol, giving 3.45 g of 5-methyl-2-(4-methylphenyl)-1H-imidazole-4-carboxylic acid, hydrazide.

A mixture of 2.9 g of the above hydrazide and 15 ml of triethoxymethane was stirred and refluxed overnight and then cooled. The solid was collected, giving 2.7 g of 5-methyl-2-(4-methylphenyl)-1H-imidazole-4-carboxylic acid, (ethoxymethylene)hydrazide.

A mixture of 2 g of this hydrazide, 470 mg of 85% potassium hydroxide and 70 ml of ethanol was stirred and refluxed overnight. The mixture was cooled, acidified with glacial acetic acid to pH 5-6 and the solid collected, giving 0.8 g of the desired product, mp 251°-253° C.

EXAMPLE 7

Preparation of 50 mg Tablets

| Per Tablet | Ingredient | Per 10,000 Tablets |
|---|---|---|
| 0.050 g | 8-Methyl-6-(3-pyridinyl)-imidazo[1,5-d]-1,2,4-triazin-1(2H)—one | 500 g |
| 0.080 g | Lactose | 800 g |
| 0.010 g | Corn starch (for mix) | 100 g |
| 0.008 g | Corn starch (for paste) | 80 g |
| 0.148 g | | 1480 g |
| 0.002 g | Magnesium stearate | 20 g |
| 0.150 g | | 1500 g |

The 8-methyl-6-(3-pyridinyl)imidazo[1,5-d]-1,2,4-triazin-1(2H)-one, lactose and corn starch for mix are blended together. The corn starch (for paste) is suspended in 600 ml of water and heated with stirring to form a paste. This paste is then used to granulate the mixed powders. The wet granules are screened, dried at 120° F. and then rescreened. The mixture is lubricated with magnesium stearate and compressed into tablets.

EXAMPLE 8

Preparation of Oral Suspension

| Ingredient | Amount |
|---|---|
| 8-Methyl-4-propylimidazo[1,5-d]-1,2,4-triazin-1(2H)—one | 500 mg |
| Sorbitol solution (70% N.F.) | 40 ml |
| Sodium benzoate | 150 mg |
| Saccharin | 10 mg |
| Red dye | 10 mg |
| Cherry flavor | 50 mg |
| Water qs | 100 ml |

The sorbitol solution is added to 40 ml of water and the 8-methyl-4-propylimidazo[1,5-d]-1,2,4-triazin-1(2H)-one is suspended therein. The saccharin, sodium benzoate, flavor and dye are added and dissolved. The volume is adjusted to 100 ml with water. Each ml of suspension contains 5 mg of active compound.

I claim:

1. A method of treating hypertension in a mammal which comprises administering to said mammal a hypotensive amount of a compound selected from those of the formula:

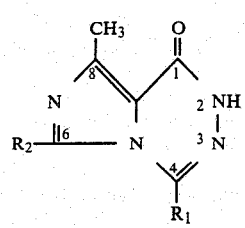

wherein $R_1$ is selected from the group consisting of hydrogen and alkyl($C_1$–$C_3$) and $R_2$ is selected from the group consisting of hydrogen, 2-pyridinyl, 3-pyridinyl, 1-naphthalenyl and 4-methylphenyl.

2. A method according to claim 1, wherein the compound is 4-ethyl-8-methylimidazo[1,5-d]-1,2,4-triazin-1(2H)-one.

3. A method according to claim 1, wherein the compound is 8-methyl-4-propylimidazo[1,5-d]-1,2,4-triazin-1(2H)-one.

4. A method according to claim 1, wherein the compound is 8-methyl-6-(3-pyridinyl)imidazo[1,5-d]-1,2,4-triazin-1(2H)-one.

5. A method according to claim 1, wherein the compound is 8-methyl-6-(1-naphthalenyl)imidazo[1,5-d]-1,2,4-triazin-1(2H)-one.

6. A method according to claim 1, wherein the compound is 8-methyl-6-(2-pyridinyl)imidazo[1,5-d]-1,2,4-triazin-1(2H)-one.

7. A method according to claim 1, wherein the compound is 8-methyl-6-(4-methylphenyl)imidazo[1,5-d]-1,2,4-triazin-1(2H)-one.

8. A compound selected from those of the formula:

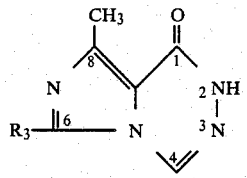

wherein $R_3$ is selected from the group consisting of 2-pyridinyl, 3-pyridinyl, 1-naphthalenyl and 4-methylphenyl.

9. The compound according to claim 8, 8-methyl-6-(3-pyridinyl)imidazo[1,5-d]-1,2,4-triazin-1(2H)-one.

10. The compound according to claim 8, 8-methyl-6-(1-naphthalenyl)imidazo[1,5-d]-1,2,4-triazin-1(2H)-one.

11. The compound according to claim 8, 8-methyl-6-(2-pyridinyl)imidazo[1,5-d]-1,2,4-triazin-1(2H)-one.

12. The compound according to claim 8, 8-methyl-6-(4-methylphenyl)imidazo[1,5-d]-1,2,4-triazin-1(2H)-one.

13. A process for producing a compound of the formula:

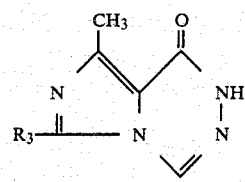

where $R_3$ is selected from 2-pyridinyl, 3-pyridinyl, 1-naphthalenyl and 4-methylphenyl, which comprises reacting a methylamine of the formula $R_3CH_2NH_2$, where $R_3$ is as described above, with 2,3-dioxobutyric acid, ethyl ester, (Z)-2-oxime at reflux temperature giving a compound of the formula:

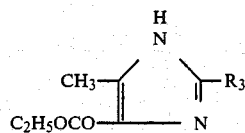

which is reacted with anhydrous hydrazine giving a compound of the formula:

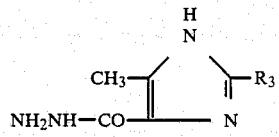

which is then reacted with triethoxymethane at reflux temperature giving the desired products.

* * * * *